(12) United States Patent
Nedestam

(10) Patent No.: US 8,558,052 B2
(45) Date of Patent: Oct. 15, 2013

(54) METHOD FOR PROVIDING A PIECE OF A FILM OF A MAGNETOELASTIC MATERIAL WITH AN ENCHANCED BENDING STIFFNESS, PRODUCT OBTAINED BY THE METHOD AND SENSOR

(75) Inventor: Stefan Nedestam, Mölnlycke (SE)

(73) Assignee: SCA Hygiene Products AB, Göteborg (SE)

( * ) Notice: Subject to any disclaimer, the term of this patent is extended or adjusted under 35 U.S.C. 154(b) by 919 days.

(21) Appl. No.: 12/308,070

(22) PCT Filed: Jun. 8, 2006

(86) PCT No.: PCT/SE2006/000675
§ 371 (c)(1),
(2), (4) Date: Dec. 5, 2008

(87) PCT Pub. No.: WO2007/142561
PCT Pub. Date: Dec. 13, 2007

(65) Prior Publication Data
US 2009/0198202 A1    Aug. 6, 2009

(51) Int. Cl.
*A61F 13/42* (2006.01)
(52) U.S. Cl.
USPC ........................................................ 604/361
(58) Field of Classification Search
USPC ................... 52/108; 138/128, 156; 242/538
See application file for complete search history.

(56) References Cited

U.S. PATENT DOCUMENTS

| | | | |
|---|---|---|---|
| 1,922,506 A * | 8/1933 | Stokes | 493/62 |
| 3,907,193 A * | 9/1975 | Heller | 428/156 |
| 5,675,886 A | 10/1997 | Hase et al. | |
| 5,676,767 A | 10/1997 | Liu et al. | |
| 2002/0166382 A1 | 11/2002 | Bachas et al. | |
| 2003/0182878 A1* | 10/2003 | Warren | 52/108 |
| 2003/0226618 A1* | 12/2003 | Herzer et al. | 148/121 |
| 2004/0113801 A1* | 6/2004 | Gustafson et al. | 340/604 |
| 2005/0116831 A1 | 6/2005 | Zribi | |

FOREIGN PATENT DOCUMENTS

| | | |
|---|---|---|
| JP | 55-027606 | 2/1980 |
| JP | 2006-032565 | 2/2006 |
| WO | WO 2004/021944 A1 | 3/2004 |
| WO | WO 2007/073258 | 6/2007 |

OTHER PUBLICATIONS

Form PCT/ISA/210 (International Search Report) dated Jan. 24, 2007, (for PCT/SE06/000675).

(Continued)

*Primary Examiner* — Susan Su
(74) *Attorney, Agent, or Firm* — Buchanan Ingersoll & Rooney PC

(57) ABSTRACT

A method for providing a piece of a film of a magnetoelastic material having an initial bending stiffness with an enhanced bending stiffness in a first direction. According to the method, the piece is provided with at least one scored line in the first direction of the piece. Furthermore, the piece is bent along at least one of the at least one scored lines so as to provide the piece with a lasting bend in a direction transverse to the first direction, whereby an enhanced bending stiffness is provided in the first direction of the piece. Also, a product obtained by the method, a sensor and an absorbent structure and an absorbent article including the sensor.

17 Claims, 9 Drawing Sheets

(56) References Cited

OTHER PUBLICATIONS

Form PCT/ISA/237 (Written Opinion of the International Searching Authority) dated Jan. 24, 2007, (for PCT/SE06/000675).
Craig A. Grimes et al., "Thin-Film Magnetoelastic Microsensors for Remote Query Biomedical Monitoring", Biomedical Microdevices, 1999, vol. 2, No. 1, pp. 51-60, 2000 Kluwer Academic Publishers, Boston, (cited on p. 1 of the specification).

Grimes et al., "Remote Query Measurement of Pressure, Fluid-Flow Velocity, and Humidity using Magnetoelastic Thick-Film Sensors" Sensors and Actuators, (2000), vol. 84, No. 3, pp. 205-212.
Supplementary European Search Report dated Feb. 2, 2011, issued in the corresponding European Patent Application No. 06747868.5-2124.

* cited by examiner

METHOD FOR PROVIDING A PIECE OF A FILM OF A MAGNETOELASTIC MATERIAL WITH AN ENCHANCED BENDING STIFFNESS, PRODUCT OBTAINED BY THE METHOD AND SENSOR

PRIORITY

This application is a national stage application of PCT/SE2006/000675, filed on 8 Jun. 2006.

TECHNICAL FIELD

The present disclosure relates to a method for providing a piece of a film of a magnetoelastic material having an initial bending stiffness with an enhanced bending stiffness in a first direction. In addition, the present disclosure relates to a product comprising a piece of a film of a magnetoelastic material, which product is obtained by means of the method. The present disclosure relates also to a sensor comprising a piece of a film of a magnetoelastic material, which piece has an initial bending stiffness in a first direction. Furthermore, the present disclosure relates to an absorbent structure and an absorbent article comprising the sensor according to the disclosure as well as a sensoring absorbent system comprising the absorbent structure according to the disclosure.

BACKGROUND

There are many different types of absorbent articles, such as diapers, diapers of pant type, incontinence garments, sanitary napkins, bed protectors, wipes, towels, tissues, tampon-like products and wound or sore dressings, known today for absorption, retention and isolation of body wastes, such as urine, faeces and blood. Some of the known such absorbent articles comprise a sensor which responds to an event, such as urination or defecation, after absorption onto or into the absorbent article. The response may, for example, be a signal after the event has occurred and may be based on measurement of, for example, wetness, a biological analyte and/or a chemical analyte. The signal of an event enables the user, parent, care taker, nursing personnel, etc. to determine with ease that an event has occurred. One type of sensor that is utilized in some absorbent articles is the magnetoelastic sensor. Magnetoelastic sensors have been described by Grimes et al. (Biomedical Microdevices, 2:51-60, 1999).

A magnetoelastic sensor comprises a piece, typically a strip, of a magnetoelastic material. Materials that are suitable to utilize as the magnetoelastic material in a magnetoelastic sensor are materials with a non-zero magnetostriction and a high magnetoelastic coupling such as, for example, iron-nickel alloys, rare earth metals, ferrites, e.g. spinel type ferrites ($Fe_3O_4$, $MnFe_2O_4$), silicon-iron alloys, many other different alloys and mixtures thereof. Soft magnetoelastic materials, alloys and mixtures thereof as well as amorphous magnetoelastic materials, alloys and mixtures thereof may be utilized. Examples of amorphous magnetoelastic alloys are metglases such as $Fe_{40}Ni_{38}Mo_4B_{18}$, e.g. Metglas 2826MB™ (Honeywell Amorphous Metals, Pittsburgh, Pa., USA), $(FeCo)_{80}B_{20}$, $(CoNi)_{80}B_{20}$ and $(FeNi)_{80}B_{20}$.

The term "magnetostriction" refers to a phenomenon whereby a material will change dimensions in the presence of an external magnetic field. The size of the dimensional change depends on the magnetization in the material and, of course, on the material properties. The phenomenon of magnetostriction is due to the interaction between the atomic magnetic moments in the material.

The term "a high magnetoelastic coupling" refers to the fact that a material having a high magnetoelastic coupling efficiently converts magnetic energy into mechanical elastic energy and vice versa. When a material that may convert magnetic energy into mechanical elastic energy is excited by a time varying magnetic field, elastic waves mechanically deform the material, which has a mechanical resonant frequency inversely proportional to its length. If the material also is magnetostrictive, it generates a magnetic flux when the material is mechanically deformed, which magnetic flux extends remotely and that may be detected by a pick-up coil.

Furthermore, a magnetoelastic material of a magnetoelastic sensor stores magnetic energy in a magnetoelastic mode when excited by an external magnetic field. When the magnetic field is switched off, the magnetoelastic material shows damped oscillation with a specific frequency denoted as the magnetoacoustic resonant frequency. These oscillations give rise to a magnetic flux that varies in time, which can be remotely detected by a pick-up coil. If a pulsed magnetic field such as, for example, a pulsed sine wave magnetic field is applied to the magnetoelastic material, it will be possible to detect a characteristic resonant frequency, i.e. the magnetoacoustic effect, between the magnetic pulses. The magnetoacoustic resonant frequency is inversely proportional to the length of the piece of magnetoelastic material. Changes in the magnetoacoustic resonant frequency may be monitored so as to measure or detect multiple environmental parameters.

WO 2004/021944 describes a disposable sensoring absorbent structure comprising at least one absorbent layer and at least one sensing device comprising a magnetoelastic film. The sensoring absorbent structure may be comprised in an absorbent article such as, for example, a diaper, a diaper of pant type, an incontinence protector, a sanitary napkin or a bed protector. In one embodiment the sensing device is intended to be utilized for detection of wetness. The magnetoelastic film of the sensing device is then coated with a wetness sensitive polymer which interacts with wetness, e.g. moisture, a liquid or humidity. The wetness sensitive polymer interacts with wetness, such as urine, through absorption or adsorption, whereby the mass of the sensing device is changed. This change in mass will either increase or decrease the magnetoacoustic resonant frequency of the magnetoelastic film. Thus, the mass change is measurable and correlates to the amount of wetness interacting with the wetness sensitive polymer. In another embodiment, the magnetoelastic film of the sensing device is coated directly or indirectly with at least one detector molecule adapted to detect at least one target biological and/or chemical analyte in body waste, body exudates or the user's/wearer's skin. WO 2004/021944 is herein incorporated by reference in its entirety.

It is known to utilize magnetoelastic elements within many other technical fields than absorbent articles. For example, it is known to utilize magnetoelastic elements in connection with position sensors, identification markers and as anti-theft tags or electronic article surveillance (EAS) tags.

Magnetoelastic materials that may be utilized as the magnetoelastic material in, for example, a magnetoelastic sensor are typically produced as continuous ribbons. However, such ribbons reveal typically a longitudinal curvature or are prone to curve in the longitudinal direction. The longitudinal curvature, or the tendency to curve in the longitudinal direction, may be production-inherent and/or may be provided due to that the ribbon is stored in a rolled form. For example, amorphous ferromagnetic metals are typically produced by rapid solidification from a melt as continuous ribbons. In such ribbons a production-inherent longitudinal curvature may be seen originating from thermally induced mechanical stresses during rapid solidification.

The fact that the ribbons of magnetoelastic material, which may be utilized for producing magnetoelastic sensors, typically present a longitudinal curvature or are prone to curve in the longitudinal direction is a common problem. Strips of such ribbons of magnetoelastic material are typically used in magnetoelastic sensors. If a ribbon of a magnetoelastic material reveals a longitudinal curvature or is prone to curve in the longitudinal direction, a strip cut from the ribbon will also reveal a longitudinal curvature or will also be prone to curve in the longitudinal direction. Usually, a magnetoelastic sensor is encapsulated or packaged in an encapsulation, a package, a housing or similar device. However, if a strip of a magnetoelastic material utilized in a magnetoelastic sensor reveals a longitudinal curvature or is prone to curve in the longitudinal direction, an encapsulation must have a relatively large height to accommodate the magnetoelastic sensor without inhibiting the oscillations of the sensor. If the magnetoelastic sensor during vibration touches the encapsulation, the magnetoacoustic resonance frequency of the sensor may be disturbed or damped. For example, in the field of absorbent articles it is of discretion reasons important that the encapsulation is as thin as possible. Thus, the fact that ribbons of a magnetoelastic material, which may be utilized for producing magnetoelastic sensors, typically reveal a longitudinal curvature or are prone to curve in the longitudinal direction causes problems with respect to the design of encapsulations. Disturbance of the oscillations of an encapsulated magnetoelastic sensor is a common problem.

Furthermore, it is common to enhance the magnetostrictive effect of the magnetoelastic material of a magnetoelastic sensor by including a magnetic bias field. For example, the magnetic bias field may be generated by a biasing element such as a permanent magnet or a permanent magnet film positioned in proximity to the magnetoelastic material. However, the magnetoelastic material and the biasing element exhibit typically a magnetic attraction for one another. Thereby, if the magnetoelastic material reveals a longitudinal curvature or is prone to curve in the longitudinal direction and if a biasing element is positioned in proximity to the magnetoelastic material, there is a risk that the magnetoelastic material will be drawn into contact with the biasing element and/or, if encapsulated, into contact with the encapsulation. Then the oscillations of the magnetoelastic material will be disturbed or damped.

A longitudinal curvature of a ribbon of a magnetoelastic material, or a tendency of a ribbon of a magnetoelastic material to curve in the longitudinal direction, may be counteracted and removed by enhancing the longitudinal bending stiffness of the ribbon. One known way of enhancing the longitudinal bending stiffness of a ribbon of a magnetoelastic material is to provide the ribbon with a transverse curvature. This is described in, for example, U.S. Pat. No. 5,676,767. In the method according to U.S. Pat. No. 5,676,767, a curling fixture is provided in an oven for the purpose of giving a transverse curvature to a ribbon of a magnetoelastic material. The ribbon is drawn longitudinally through the fixture and the fixture has a curl surface, which proceeding in a direction transverse to the longitudinal axis of the ribbon rises and the falls. The heating applied to the ribbon during its passage through the fixture causes the ribbon to conform itself to the curl surface, thereby providing the ribbon with a transverse curvature. The transverse curvature enhances the longitudinal bending stiffness of the ribbon and counteracts any longitudinal curvature or tendency to curve in the longitudinal direction. Thereby, the transverse curvature reduces the above mentioned problems with disturbance or dampening of the oscillations of the magnetoelastic material and the above mentioned problems with the encapsulation design. However, this method requires that a heat treatment is applied to the magnetoelastic material in order to enhance the longitudinal bending stiffness. In addition, this method requires the use of a fixture and that the magnetoelastic material is drawn through the fixture. Furthermore, when a magnetoelastic sensor coated with a polymer such as, for example, a wetness sensitive polymer, is to be produced, this method requires an extra process step before the polymer may be coated on the magnetoelastic material.

OBJECTS AND SUMMARY

One object is to provide an improved method for providing a piece of a film of a magnetoelastic material having an initial bending stiffness with an enhanced bending stiffness in a first direction.

This object is achieved in accordance with a method that comprises the steps of:
  providing said piece with at least one scored line in said first direction of said piece, and
  bending said piece along at least one of said at least one scored lines so as to provide said piece with a lasting bend in a direction transverse to said first direction, whereby an enhanced bending stiffness is provided in said first direction of said piece.

In a further aspect, there is provided a product comprising a piece of a film of a magnetoelastic material, which product is produced by the above method.

Another object is to provide an improved sensor comprising a piece of a film of a magnetoelastic material, which piece has an initial bending stiffness in a first direction. This object is achieved in accordance with a piece that is provided with at least one scored line in a first direction of said piece and that said piece is bent along at least one of said at least one scored lines such that said piece is provided with a lasting bend in a direction transverse to said first direction, whereby an enhanced bending stiffness is provided in said first direction of said piece.

Still other objects and features of the present disclosure will become apparent from the following detailed description considered in conjunction with the accompanying drawings. It is to be understood, however, that the drawings are designed solely for purposes of illustration and not as a definition of the limits of the disclosure. It should be further understood that the drawings are not necessarily drawn to scale and that, unless otherwise indicated, they are merely intended to conceptually illustrate the structures described herein.

BRIEF DESCRIPTION OF THE DRAWINGS

In the drawings, wherein like reference characters denote similar elements throughout the several views:

FIG. 2b shows a schematic cross-sectional view of the strip shown in FIG. 2a;

DETAILED DESCRIPTION OF PREFERRED EMBODIMENTS

Figure 1A:
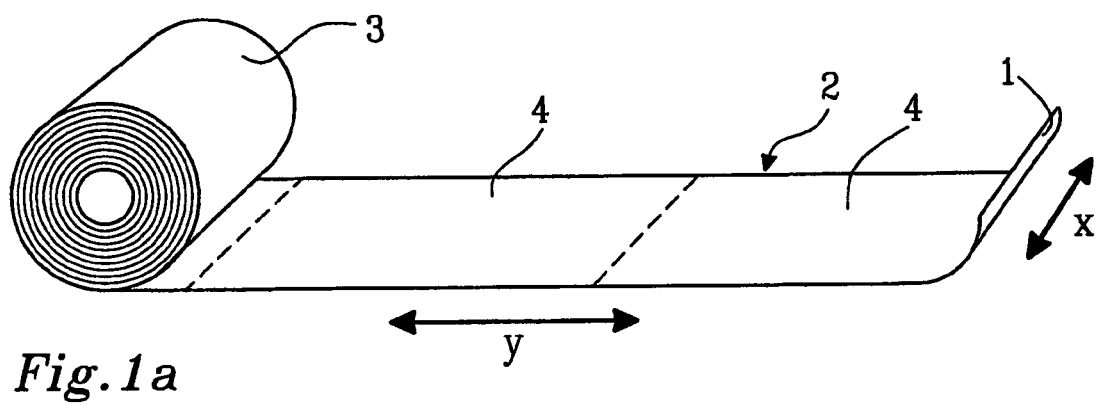
FIG. 1a shows a schematic perspective view of a film of a magnetoelastic material that may be utilized as the magnetoelastic material in a magnetoelastic sensor.
Figure 1B:
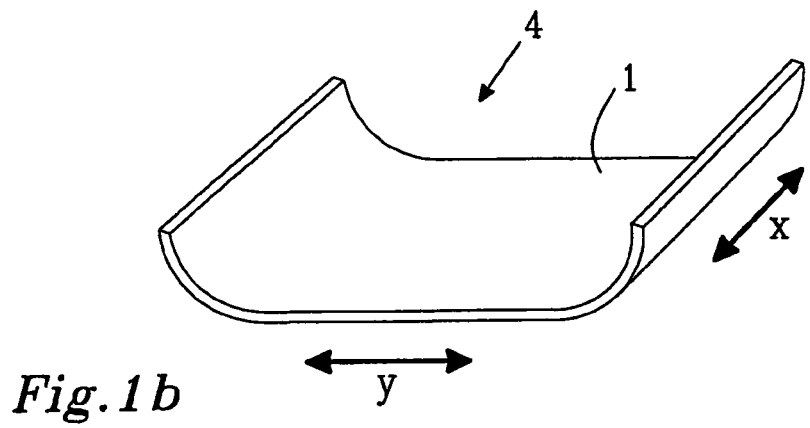
FIG. 1b shows a schematic perspective view of one example of a strip having a longitudinal curvature, which strip has been separated from the ribbon shown in FIG. 1a without further processing of the ribbon before the separation.

FIG. 1a shows a schematic perspective view of a film 1 of a magnetoelastic material that may be utilized as the magnetoelastic material in, for example, a magnetoelastic sensor. The film 1 of a magnetoelastic material shown in FIG. 1a is provided in the form of a ribbon 2 having a transverse direction x and a longitudinal direction y. The ribbon 2 is stored in the form of a roll 3. The ribbon 2 may be seen as being constituted by a number of pieces having the shape of strips 4 in the longitudinal direction, which strips 4 are not yet separated or marked. The boundaries of the respective strips 4 are indicated by dashed lines in FIG. 1a. Furthermore, the ribbon 2 reveals a longitudinal curvature, which is schematically shown in FIG. 1a. As above described, a ribbon of a magnetoelastic material that may be utilized as the magnetoelastic material in, for example, a magnetoelastic sensor reveals typically a longitudinal curvature or is prone to curve in the longitudinal direction. The longitudinal curvature, or the tendency to curve in the longitudinal direction, may be production-inherent and/or may be provided due to that the ribbon is stored in a rolled form. The term "longitudinal curvature" is herein intended to mean a curvature which has an extension in the longitudinal direction of a film of a magnetoelastic material. Thus, a ribbon of a film of a magnetoelastic material that reveals a longitudinal curvature reveals a curvature in the longitudinal direction of the ribbon, i.e. the ribbon is curved in the longitudinal direction. A strip that is separated from a ribbon, which reveals a longitudinal curvature or is prone to curve in the longitudinal direction, will also reveal a longitudinal curvature or be prone to curve in the longitudinal direction if no further processing of the ribbon is performed before the separation. FIG. 1b shows a schematic perspective view of one example of one of the strips 4 constituting the ribbon 2 after it has been separated from the ribbon 2. The strip 4 shown in FIG. 1b has been separated from the ribbon 2 shown in FIG. 1a without further processing of the ribbon 2 before the separation. The strip 4 has a transverse direction x and a longitudinal direction y.

The present disclosure provides a method for providing a piece of a film of a magnetoelastic material having an initial or inherent bending stiffness with an enhanced bending stiffness in a first direction. The method according to an embodiment the disclosure comprises the steps of:

providing the piece with at least one scored line in the first direction of the piece, and bending the piece along at least one of the at least one scored lines so as to provide the piece with a lasting bend in a direction transverse to the first direction, whereby an enhanced bending stiffness is provided in the first direction of the piece.

The magnetoelastic material of the piece, to which the method according to the disclosure may be applied, may be any known magnetoelastic material. For example, it may be applied to any magnetoelastic material with a non-zero magnetostriction and a high magnetoelastic coupling. Examples of such magnetoelastic materials are iron-nickel alloys, rare earth metals, ferrites, e.g. spinel type ferrites ($Fe_3O_4$, $MnFe_2O_4$), silicon-iron alloys, many other different alloys and mixtures thereof. Furthermore, the method according to the disclosure may be applied to, for example, soft magnetoelastic materials, alloys and mixtures thereof as well as amorphous magnetoelastic materials, alloys and mixtures thereof. Examples of amorphous magnetoelastic alloys are metglases such as $Fe_{40}Ni_{38}Mo_4B_{18}$, e.g. Metglas 2826MB™ (Honeywell Amorphous Metals, Pittsburgh, Pa., USA), $(FeCo)_{80}B_{20}$, $(CoNi)_{80}B_{20}$ and $(FeNi)_{80}B_{20}$.

Furthermore, the method according to the disclosure may be applied to a piece having the shape of a strip, a ribbon or any other shape. The piece, to which the method according to the disclosure is applied, may be an integral part of a ribbon or may be a separate piece. Furthermore, the method according to the disclosure may be applied to a piece being an integral part of a ribbon stored in a rolled form or any other form. For example, the method according to the disclosure may be applied to the ribbon 2 shown in FIG. 1a, to one of the strips 4 being an integral part of the ribbon 2 shown in FIG. 1a or to the strip 4 shown in FIG. 1b.

Different embodiments of the method according to the disclosure will now be described when applied to the piece 4 of a film 1 of a magnetoelastic material having the shape of a strip shown in FIG. 1b for providing the strip 4 with an enhanced bending stiffness in the longitudinal direction, i.e. in a first direction.

Figure 2A:
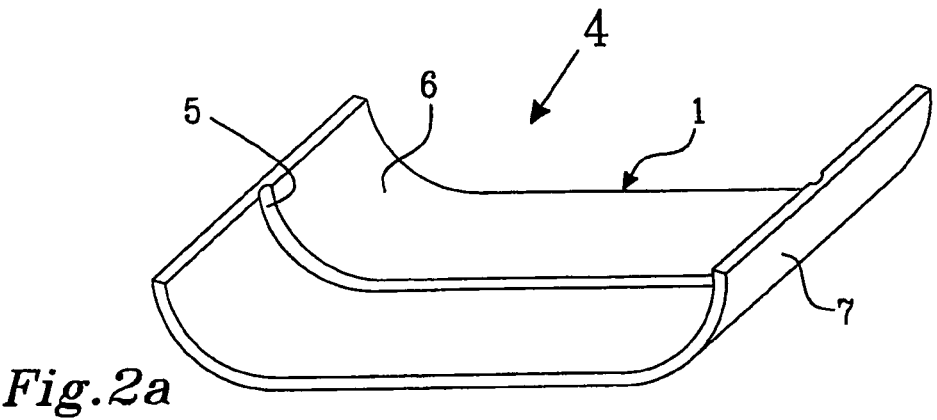
FIG. 2a shows a schematic perspective view of a strip after an initial step of a first embodiment of the method according to the disclosure.
Figure 2B:
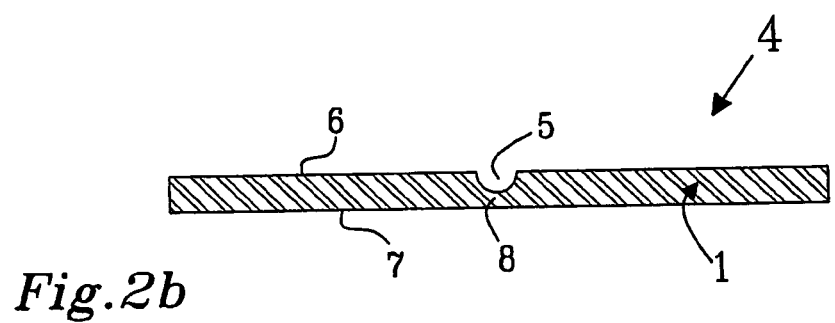

In an initial step of a first embodiment of the method according to the disclosure, the strip 4 is provided with a scored line/notch/slit 5 in the longitudinal direction on a first side 6 of the strip 4. Thus, the strip 4 is then provided with a scored line 5 extending in the longitudinal direction of the strip 4. In the first embodiment the scored line 5 is provided essentially centralized on the strip 4, i.e. it is provided essentially in the middle of the strip 4. FIG. 2a shows a schematic perspective view of the strip 4 after the initial step of providing the strip 4 with a scored line 5. FIG. 2b shows a schematic cross-sectional view of the strip 4 shown in FIG. 2a.

The depth of the scored line 5 is less than the thickness of the film 1 of the strip 4, i.e. the scored line 5 does not extend through the complete thickness of the film 1 of the strip 4. The thickness of the film 1 of a magnetoelastic material that the method according to the disclosure may be applied to is typically about 0.01-1000 µm, such as 0.01-200 µm, 5-100

µm or 0.01-100 µm. The depth of the scored line 5 may be, for example, 1-40% of the film thickness, preferably 10-20% of the film thickness.

In the first embodiment of the method according to the disclosure, the strip 4 is provided with the scored line 5 by an etching process. The utilized etching process may be any known etching process that is suitable for providing a scored line 5 in a film 1 of a magnetoelastic material. For example, the etching process may be a chemical process, an electrochemical process or an ion-beam process. Furthermore, a photoetching process combining photolithography with the etching process may also be utilized.

One non-limiting example of an etching process that may be utilized in the first embodiment of the present disclosure will now described in broad outline. In this example the strip 4 is coated on the first side 6 with a photoresist in a first step. A second side 7, i.e. the side opposite the first side 6, of the strip 4 is then also provided with a suitable cover for protection during the etching process. In a second step the photoresist is exposed to light through a mask. Depending on whether a positive or negative photoresist is utilized, the mask is designed either such that those parts of the photoresist are exposed to light that cover parts of the strip 4 where the scored line 5 is to be created, or such that those parts of the photoresist are exposed to light that do not cover parts of the strip 4 where the scored line 5 is to be created. In a third step those parts of the photoresist are removed that cover the parts of the strip 4 where the scored line 5 is to be created. Thereafter the strip 4 is etched in a fourth step by means of a suitable etchant such as, for example, an acid or ferric chloride. The remaining photoresist on the first side 6 and the cover on the second side 7 serve then as barriers against the etchant. Thereby, the strip 4 is exposed to the etchant only in those parts where the scored line 5 is to be produced. After the etching step, the remaining photoresist is removed.

The above described non-limiting example of an etching process and other etching processes suitable to utilize in the method according to the disclosure are well-known for persons skilled in the art and are therefore not further explained.

In a subsequent step of the first embodiment, the strip 4 being provided with one scored line 5 is bent along the scored line 5 so as to provide the strip 4 with a lasting bend in the transverse direction of the strip 4, i.e. in a direction transverse to the first direction. The fact that the strip 4 is provided with a lasting bend in the transverse direction implies that the strip 4 is provided with a cross-sectional shape deviating from a planar cross-sectional shape. A lasting bend or permanent bend is provided by means of the bending step due to the fact that the bending is performed such that the magnetoelastic material is at least partially plastically deformed at a bottom 8 of the scored line 5 along which the strip 4 is bent.

Figure 2C:
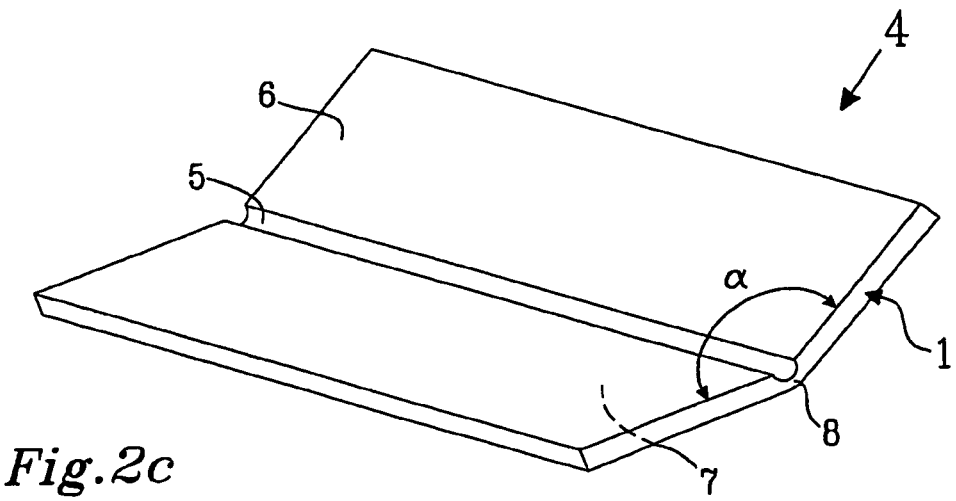
FIG. 2c shows a schematic perspective view of the strip shown in FIGS. 2a and 2b after a bending step of a first embodiment of the method according to the disclosure has been applied to the strip.
Figure 2D:
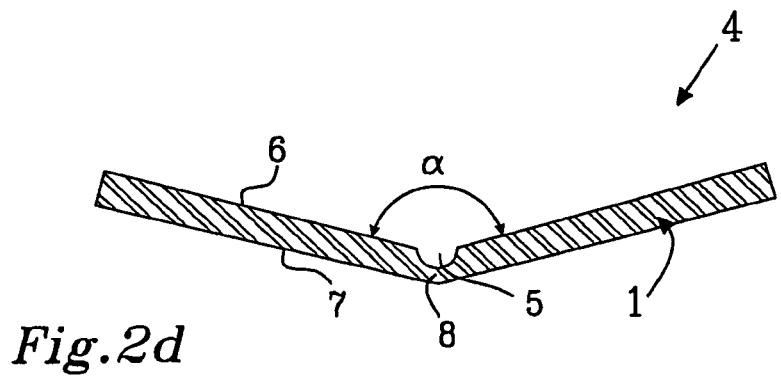
FIG. 2d shows a schematic cross-sectional view of the strip shown in FIG. 2c.
Figure 2E:
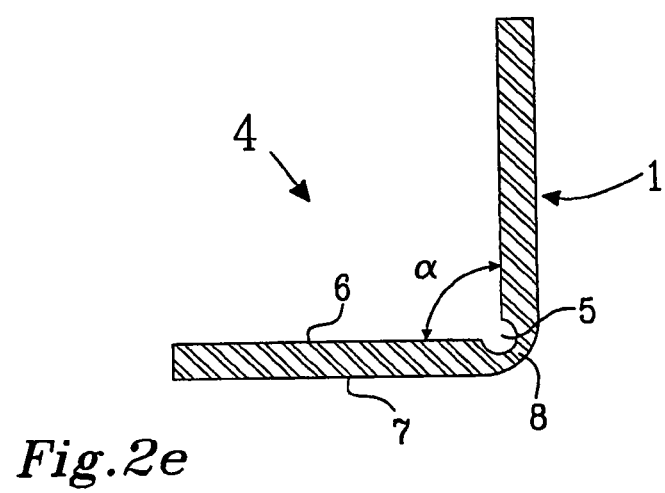
FIGS. 2e-2f show schematic cross-sectional views of the strip shown in FIGS. 2a and 2b after variants of the bending step of a first embodiment of the method according to the disclosure have been applied to the strip.
Figure 2F:
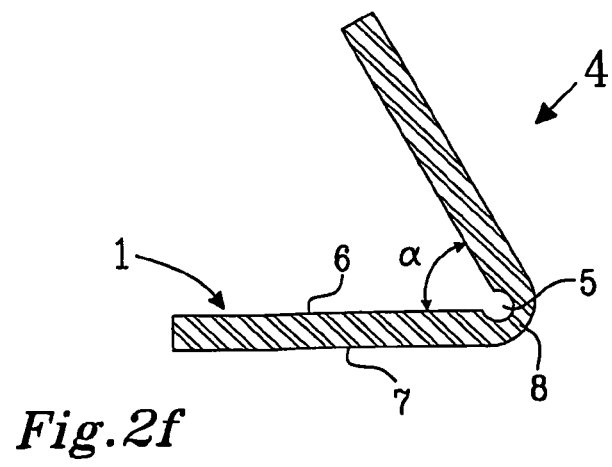

In the first embodiment, the strip 4 is bent along the scored line 5 so as to provide the strip 4 with a lasting bend being angular. After the bending step, the cross-section of the strip 4 is thereby angular. Thus, the bending of the strip 4 is in the first embodiment performed such that an angle α is enclosed. The bending in the first embodiment may be performed such that any suitable angle α within the range of 0<α<180° is enclosed. For example, the strip 4 may in the first embodiment be bent so as to provide the strip 4 with a lasting bend enclosing an angle α greater than 90° (FIGS. 2c-2d). The strip 4 may, for example, be bent such that α is 160°≤α<180°. Preferably α is 170°≤α<180°. However, the strip 4 may in the first embodiment also be bent so as to provide the strip 4 with a lasting essentially right-angular bend (FIG. 2e) or a lasting bend enclosing an angle α less than 90° such as a lasting V-shaped bend (FIG. 2f). FIG. 2c shows a schematic perspective view of the strip 4 shown in FIGS. 2a and 2b after it has been provided with a lasting bend enclosing an angle α greater than 90° and FIG. 2d shows a schematic cross-sectional view of the strip 4 shown in FIG. 2c. FIG. 2e shows a schematic cross-sectional view of the strip 4 shown in FIGS. 2a and 2b after it has been provided with a lasting essentially right-angular bend and FIG. 2f shows a schematic cross-sectional view of the strip 4 shown in FIGS. 2a and 2b after it has been provided with a lasting bend enclosing an angle less than 90°.

Furthermore, the strip 4 may be bent along the scored line 5 either such that it is bent towards or away from the scored line 5.

Since the strip 4 is provided with a lasting bend in the transverse direction of the strip 4, an enhanced bending stiffness is provided in the longitudinal direction of the strip 4. The enhanced bending stiffness achieved will counteract and/or remove any curvature of the strip 4 in the longitudinal direction, or any tendency to curve in the longitudinal direction, which may be production-inherent and/or provided due to that films 1 of magnetoelastic materials are stored in a rolled form.

Preferably, the bending is performed by means of a mould, or in a mould, such that a controlled bending of the strip 4 is achieved. For example, the mould utilized may comprise a bending surface, which has such a shape such that the strip 4 may be bent along the scored line 5 and may be given a desired bend in the transverse direction when it is pressed at least partially against the bending surface. The strip 4 may be pressed against the bending surface by means of any suitable means. For example, it may be pressed against the bending surface by means of a second mould having a second bending surface. The strip 4 is then positioned between the two bending surfaces of the two moulds during the bending. The second bending surface has then such a shape such that it also contributes to bending the strip 4 along the scored line 5 and to giving the strip 4 a desired bend in the transverse direction. Furthermore, instead of utilizing one or more moulds for the bending, the strip 4 may be bent between two rolls having bending surfaces such that a desired bending is achieved.

Figure 2G:
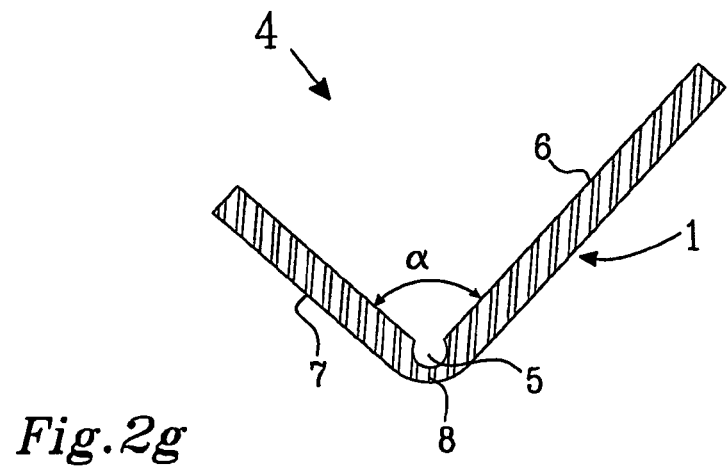
FIG. 2g shows a schematic cross-sectional view of a strip after a second embodiment of the method according to the disclosure has been applied to the strip.

A second embodiment of the method according to the disclosure corresponds to the first embodiment except for that the scored line 5 is not provided such that it is centralized on the strip 4. Instead the scored line 5 is provided on the strip 4 such that it is positioned at a shorter distance to one of the longitudinal side edges of the strip 4 than to the other of the longitudinal side edges. The bending step in the second embodiment is performed such that any suitable angular bend is achieved, i.e. such that any suitable angle α within the range of 0<α<180° is enclosed. For example, the bending step in the second embodiment may be performed so as to provide the strip 4 with a lasting bend enclosing an angle α greater than 90° (not shown). The strip 4 may, for example, be bent such that α is 160°≤α<180°. Preferably α is 170°≤α<180°. However, the strip 4 may in the second embodiment also be bent so as to provide the strip 4 with a lasting essentially right-angular bend (FIG. 2g) or a lasting bend enclosing an angle α less than 90° (not shown). Furthermore, the scored line 5 may in the second embodiment be provided at such a position on the strip 4 and the strip 4 may be bent so as to provide the strip 4 with a lasting L-shaped bend. FIG. 2g shows a schematic cross-sectional view of a strip 4 being provided with an essentially right-angular bend, which is L-shaped.

A third embodiment of the method according to the present disclosure corresponds to the first embodiment except for that the first side 6 is provided with more than one scored line 5, i.e. it is provided with two or more scored lines 5 extending in the longitudinal direction of the strip 4. The scored lines 5 may in the third embodiment be provided at any suitable positions and at any distance from each other or from any of the longitudinal side edges, so as to be positioned such that a desired shape of the bend may be achieved when the strip 4 is bent along the scored lines 5 in the bending step.

Figure 2H:
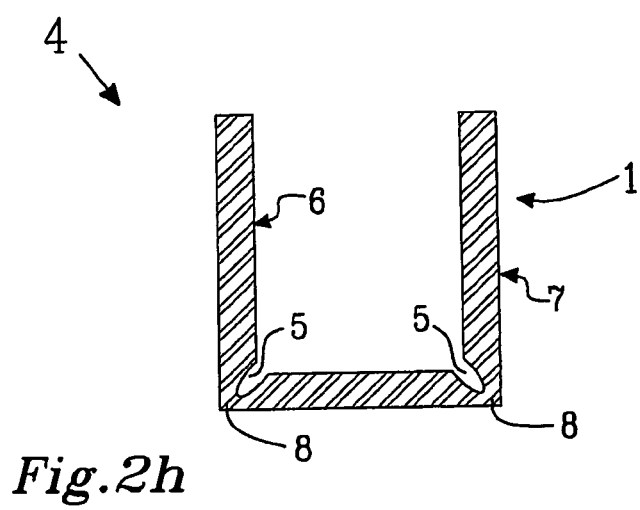
FIGS. 2h-2k show schematic cross-sectional views of a strip after variants of a third embodiment of the method according to the disclosure have been applied to the strip.
Figure 2I:
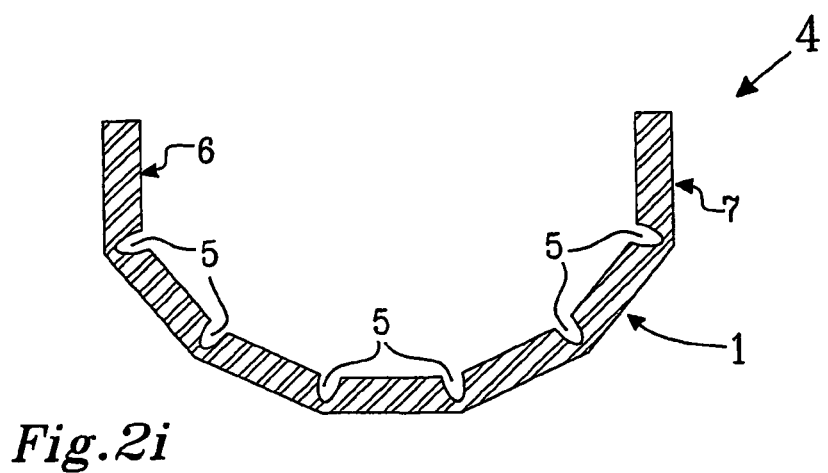
Figure 2J:
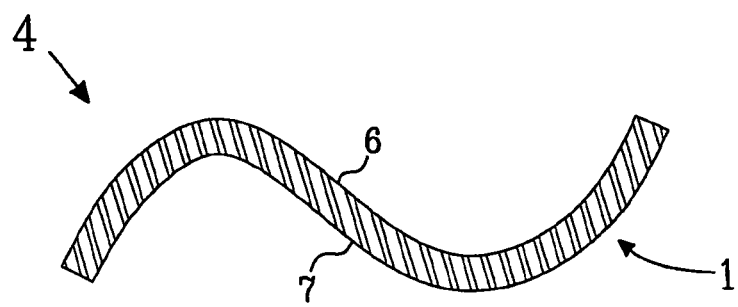
Figure 2K:
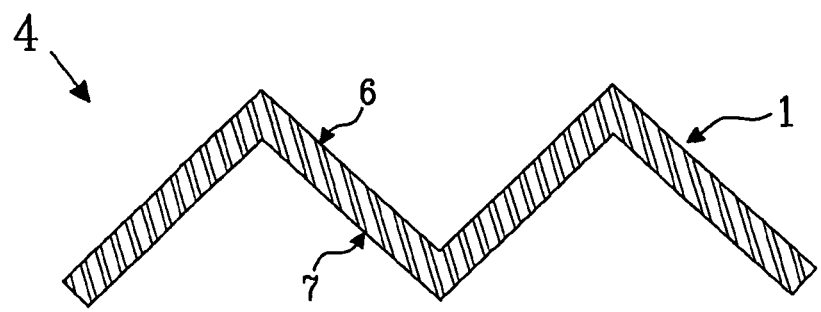

For example, the strip 4 may in the third embodiment be provided with two scored lines 5 and the strip 4 may be bent along the two scored lines 5 in the bending step such that a cup-shaped bend is achieved. A cross-sectional view of one example of a strip 4 after such a variant of the third embodiment is shown in FIG. 2h. Another alternative is that the strip 4 in the third embodiment is provided with several scored lines 5 on the first side 6 and that the strip 4 is bent along the several scored lines 5 such that a curve-shaped bend is achieved. For example, a bend may then be achieved that forms a part of a circle or that is U-shaped. A cross-sectional view of one example of a strip 4 after such a variant of the third embodiment is shown in FIG. 2i. Thus, by providing several scored lines 5 on the first side 6 of the strip 4 and bending the strip 4 along the several scored lines 5 it is possible to provide the strip 4 with a transverse curvature. The term "transverse curvature" is herein intended to mean a curvature which has an extension in the transverse direction of a film 1 of a magnetoelastic material. Thus, a strip 4 of a film 1 of a magnetoelastic material that reveals a transverse curvature reveals a curvature in the transverse direction of the strip 4, i.e. the strip 4 is curved in the transverse direction. Furthermore, the strip 4 may in the third embodiment be provided with several scored lines 5 on the first side 6 and be bent along the several scored lines 5 such that an S-shaped bend (FIG. 2j) or a wave-shaped bend (FIG. 2k) is achieved. Cross-sectional views of examples a strip 4 after such variants of the third embodiment are shown in FIG. 2j and FIG. 2k. The scored lines 5 are omitted in FIGS. 2j and 2k for clarity reasons.

A fourth embodiment of the method according to the disclosure corresponds to any of the above described embodiments except for that one or more scored lines 5 is/are provided on each side 6, 7 of the strip 4, i.e. at least one scored line 5 is provided on the first side 6 and at least one scored line 5 is provided on the second side 7.

As may be realized from the above, any suitable number of scored lines 5 may be provided on the strip 4, at any suitable positions on the strip 4, in the method according to embodiments of the disclosure so as to enable bending of the strip 4 such that a shape of the lasting bend is achieved that enhances the longitudinal bending stiffness of the strip 4. Furthermore, an active bending is not required along all provided scored lines 5 in the method according to the disclosure, i.e. scored lines 5 may be provided along which the strip 4 is not bent.

Even if different embodiments of the method according to the disclosure have been described when applied to a piece of a film 1 of a magnetoelastic material having the shape of a strip and being a separate piece, the described embodiments may also be applied to a piece of a film 1 of a magnetoelastic material having any other shape or to a piece being an integral part of, for example, a ribbon. Thus, any of the above described embodiments of the method according to the disclosure may, for example, be applied to one of the strips 4 constituting the ribbon 2 shown in FIG. 1a. Then the strip 4, to which the method is applied, is optionally separated from the ribbon 2 between the step of providing one or more scored lines 5 on the strip 4 and the step of bending. For example, the strip 4 may then be separated from the ribbon 2 in a step of cutting following the step of providing one or more scored lines 5 on the strip 4. Alternatively, if etching is utilized for providing one or more scored lines 5 on the strip 4, the step of etching may then optionally be performed such that the strip 4 not only is provided with one or more scored lines 5 in the etching process but also such that the strip 4 is separated from the ribbon 2 in the etching process. Then the ribbon 2 is etched in the areas where the scored line(s) 5 is/are to be created and along one or more separation lines, i.e. along one or more lines where the strip 4 is to be separated from the ribbon 2. Along the separation line(s) the ribbon 2 is etched through such that the strip 4 is separated from the ribbon 2.

Furthermore, even if the method according to the disclosure has been described for providing a piece of a film of a magnetoelastic material with an enhanced bending stiffness in the longitudinal direction, the method according to the disclosure may be applied for providing a film of a magnetoelastic material with an enhanced bending stiffness in any other desired direction. The scored line(s) 5 is/are then provided in the direction in which an enhanced bending stiffness is desired. In addition, the method according to the disclosure may be applied to a piece of a film of a magnetoelastic material revealing a curvature in any direction or being essentially plane.

Furthermore, the piece of a film of a magnetoelastic material, to which the method is applied, may be coated at least partially with a wetness sensitive polymer on one of the first and second sides 6, 7 or be coated directly or indirectly on one of the first and second sides 6, 7 with at least one detector molecule adapted to detect at least one target biological and/or chemical analyte. Then the piece is preferably provided with one or more scored lines 5 only on the side 6, 7 that is not coated with the wetness sensitive polymer or any detector molecule(s). Furthermore, if etching is utilized for providing one or more scored lines 5 on the piece, the wetness sensitive polymer or the detector molecule(s) is/are then provided with a cover for protection during the step of etching. Examples of wetness sensitive polymers, detector molecules as well as biological and chemical analytes that the detector molecules may be adapted to detect are given below.

In variants of any of the above described embodiments of the method according to the disclosure, the piece of a film of a magnetoelastic material is provided with one or more scored lines through scribing instead of etching.

When any of the above described embodiments of the method according to the disclosure is applied to a piece of a film of a magnetoelastic material, a product comprising a piece of a film of a magnetoelastic material is obtained. The product may, for example, be utilized as a sensor or in a sensor. If the piece of a film of a magnetoelastic material is not coated with any additional layer, such as a layer of a wetness sensitive polymer, or any detector molecules, the product obtained when the method according to the disclosure is applied to the piece may be comprised in, for example, identification markers, position sensors, anti-theft tags or electronic article surveillance (EAS) tags.

Figure 3A:
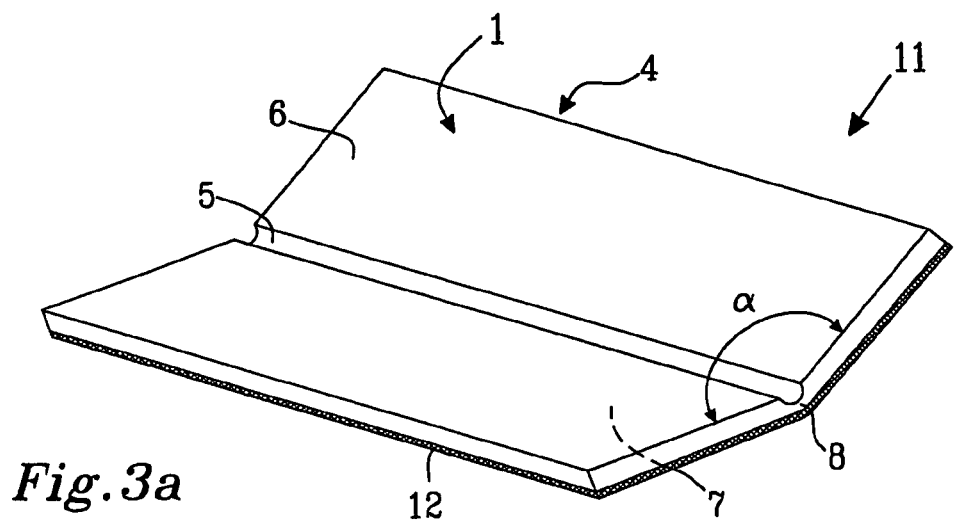
FIG. 3a shows a schematic perspective view of a first embodiment of a sensor according to the disclosure.

Furthermore, the present disclosure provides a sensor comprising a film of a magnetoelastic material. The sensor according to the disclosure may be obtained by utilizing the method according to the disclosure or any other method yielding the same result. FIG. 3a shows a schematic perspective view of a first embodiment of a sensor 11 according to the disclosure.

The first embodiment of the sensor 11 according to the disclosure comprises a strip 4 of a film 1 of a magnetoelastic material. The magnetoelastic material of the strip 4 may be any known magnetoelastic material. For example, it may be any magnetoelastic material with a non-zero magnetostriction and a high magnetoelastic coupling. Examples of such magnetoelastic materials are iron-nickel alloys, rare earth metals, ferrites, e.g. spinel type ferrites ($Fe_3O_4$, $MnFe_2O_4$), silicon-iron alloys, many other different alloys and mixtures thereof. Furthermore, the magnetoelastic material may be any material selected from the group of soft magnetoelastic materials, alloys and mixtures thereof as well as amorphous magnetoelastic materials, alloys and mixtures thereof. Examples of amorphous magnetoelastic alloys are metglases such as $Fe_{40}Ni_{38}Mo_4B_{18}$, e.g. Metglas 2826MB™ (Honeywell Amorphous Metals, Pittsburgh, Pa., USA), $(FeCo)_{80}B_{20}$, $(CoNi)_{80}B_{20}$ and $(FeNi)_{80}B_{20}$. The thickness of the film 1 of a magnetoelastic material is typically about 0.01-1000 μm, such as 0.01-200 μm, 5-100 μm or 0.01-100 μm. The film 1 of a magnetoelastic material has an initial or inherent bending stiffness.

The strip 4 shown in FIG. 3a is provided with a scored line/notch/slit 5 in the longitudinal direction, i.e. in a first direction, on a first side 6. Thus, the strip 4 is provided with a scored line 5 extending in the longitudinal direction. The scored line 5 is provided essentially centralized on the strip 4, i.e. it is provided essentially in the middle of the strip 4. The depth of the scored line 5 is less than the thickness of the film 1 of the strip 4, i.e. the scored line 5 does not extend through the complete thickness of the film 1 of the strip 4. The depth of the scored line 5 may be, for example, 1-40% of the film thickness, preferably 10-20% of the film thickness. Furthermore, the strip 4 is bent along the scored line 5 such that the strip 4 is provided with a lasting or permanent bend in the transverse direction of the strip 4, i.e. in a direction transverse to the first direction. The bend is a lasting or permanent bend due to that the magnetoelastic material is at least partially plastically deformed at a bottom 8 of the scored line 5 along which the strip 4 is bent. The fact that the strip 4 is provided with a bend in the transverse direction implies that the strip 4 is provided with a cross-sectional shape deviating from a planar cross-sectional shape.

Furthermore, the bend of the strip 4 shown in FIG. 3a is angular, whereby the cross-section of the strip 4 is angular. More specifically, the bend of the strip 4 shown in FIG. 3a encloses an angle α that is greater than 90°.

Since the strip 4 is provided with a lasting bend in the transverse direction of the strip 4, an enhanced bending stiffness, i.e. a bending stiffness that is greater than an initial or inherent bending stiffness of the strip 4, is provided in the longitudinal direction of the strip 4. The enhanced bending stiffness achieved will counteract and/or remove any curvature of the strip 4 in the longitudinal direction, or any tendency to curve in the longitudinal direction, which may be production-inherent and/or provided due to that films 1 of magnetoelastic materials are stored in rolled forms.

Furthermore, the strip 4 shown in FIG. 3a is coated at least partially with a layer 12 of wetness sensitive polymer on a second side 7, i.e. the side opposite the first side 6, which wetness sensitive polymer is selected from the group consisting of linear and hydrophilic polymers or chemically/physically cross-linked swellable polymer gels based on polyvinyl alcohol, polyvinyl pyrrolidone, polyethylene oxide and co-polymers thereof, polyurethane, polyamides, starch and derivatives thereof, cellulose and derivative thereof, polysaccharides, proteins, polyacrylonitrile, polyethylene imine, acrylate based polymers, and mixtures thereof.

The wetness sensitive polymer may interact with wetness such as a liquid, humidity or moisture through, for example, absorption or adsorption. When the wetness sensitive polymer interacts with wetness, the mass of the first embodiment of the sensor 11 is changed resulting in a change of the resonant frequency, e.g. the magnetoacoustic resonant frequency, of the sensor 11. The change of the magnetoacoustic resonant frequency is detectable and correlates to the amount of wetness that the wetness sensitive polymer has interacted with, i.e. it correlates, for example, to the amount of wetness absorbed or adsorbed by the wetness sensitive polymer. Thus, the sensor 11 shown in FIG. 3a may be utilized as a wetness sensor. For example, it may be utilized for detecting body discharges such as body fluids, body waste or body exudates, i.e. urine, faeces, blood, menstruation blood, fluid matters from wounds and sores, rinsing fluid and saliva.

Figure 3B:
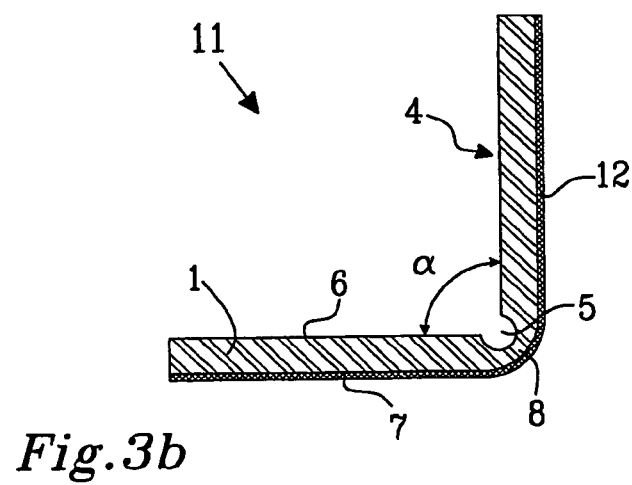
FIGS. 3b-3c show schematic cross-sectional views of variants of the first embodiment of the sensor according to the disclosure.
Figure 3C:
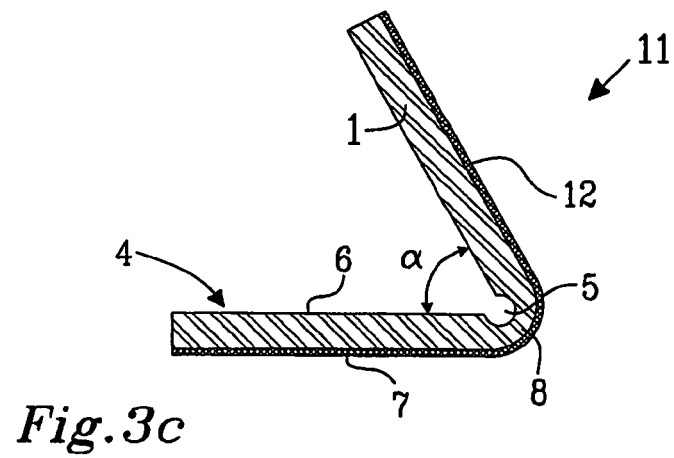

Even if the bend shown in FIG. 3a is shown as enclosing a specific angle α, the bend of the strip 4 of the sensor 11 according to the first embodiment may enclose any suitable angle α within the range of 0°<α<180°. Thereby the bend of a strip 4 of a sensor 11 according to the first embodiment may enclose an angle α that is greater than 90° (FIG. 3a). The strip 4 may, for example, be bent such that α is 160°≤α<180°. Preferably α is 170°≤α<180°. However, the bend of the strip 4 of the sensor 11 according to the first embodiment may also enclose an essentially right angle, whereby the bend is right-angular (FIG. 3b), or an angle α that is less than 90° (FIG. 3c). FIG. 3b shows a schematic cross-sectional view of a sensor 11 according to the first embodiment in which the strip 4 is provided with a right-angular bend. FIG. 3c shows a schematic cross-sectional view of a sensor 11 according to the first embodiment in which the strip 4 is provided with a bend enclosing an angle α that is less than 90°.

Furthermore, the strip 4 of the first embodiment of the sensor 11 according to the disclosure may be bent along the scored line 5 either such that it is bent towards or away from the scored line 5.

Figure 3D:
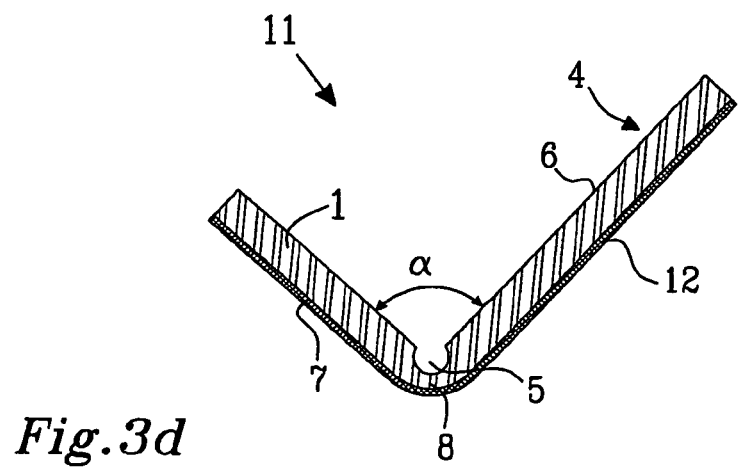
FIG. 3d shows a schematic cross-sectional view of a second embodiment of the sensor according to the disclosure.

A second embodiment of the sensor 11 according to the disclosure corresponds to the first embodiment of the sensor 11 except for the fact that the scored line 5 is not provided such that it is centralized on the strip 4. Instead the scored line 5 is provided on the strip 4 such that it is positioned at a shorter distance to one of the longitudinal side edges of the strip 4 than to the other of the longitudinal side edges. The lasting bend of the strip 4 of the sensor 11 according to the second embodiment is angular and may enclose any suitable angle α within the range of 0°<α<180°. For example, a strip 4 of a sensor 11 according to the second embodiment may be provided with a lasting bend enclosing an angle α more than 90° (not shown). The strip 4 may, for example, be bent such that α is 160°≤α<180°. Preferably α is 170°≤α<180°. However, a strip 4 of a sensor 11 according to the second embodiment may also be provided with a lasting essentially right-angular bend (FIG. 3d) or a lasting bend enclosing an angle α less than 90° (not shown). Furthermore, the scored line 5 may be provided at such a position on the strip 4 and the strip 4 may be bent such that the strip 4 is provided with a lasting L-shaped bend. FIG. 3d shows a schematic cross-sectional view of a second embodiment of a sensor 11 according to the disclosure, in which the strip 4 is provided with a lasting L-shaped bend.

Figure 3E:
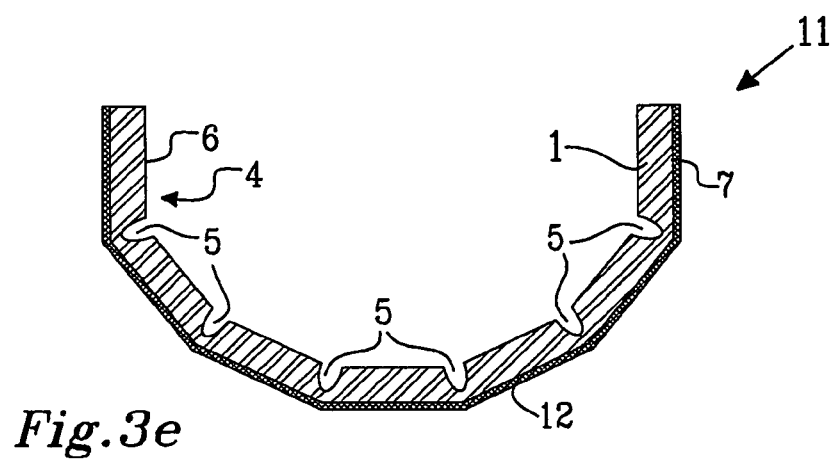
FIGS. 3e-3f show schematic cross-sectional views of variants of a third embodiment of the sensor according to the disclosure.
Figure 3F:
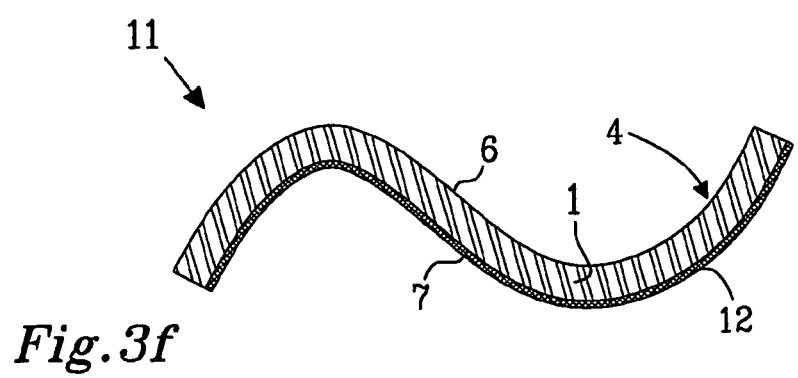

A third embodiment of the sensor 11 according to the disclosure corresponds to the first embodiment of the sensor 11 except for the fact that the first side 6 of the strip 4 is provided with more than one scored line 5, i.e. it is provided with two or more scored lines 5 extending in the longitudinal direction of the strip 4. The scored lines 5 may in the third embodiment be provided at any suitable positions and at any distance from each other or from any of the longitudinal side edges. The strip 4 is bent along the scored lines 5 in the third embodiment such that the strip 4 is provided with a lasting bend having any suitable shape. For example, the strip 4 may in the third embodiment of the sensor 11 be provided with two scored lines 5 and the strip 4 may be bent along the two scored lines 5 such that the strip 4 is provided with a cup-shaped bend (not shown). Another alternative is that the strip 4 in the third embodiment of the sensor 11 is provided with several scored lines 5 on the first side 6 and that the strip 4 is bent along the several scored lines 5 such that the strip 4 is provided with a curve-shaped bend. For example, the bend may then form a part of a circle or be U-shaped. Thus, the strip 4 may in the third embodiment of the sensor 11 be provided with a transverse curvature. A cross-sectional view of one example of a sensor 11 according to the third embodiment, in which the strip 4 is provided with a curve-shaped bend, is shown in FIG. 3e. Furthermore, the strip 4 may in the third embodiment of the sensor 11 according to the disclosure be provided with several scored lines 5 on the first side 6 and be bent along the several scored lines 5 such that an S-shaped or wave-shaped bend is provided. A schematic cross-sectional view of one example of a sensor 11 according to the third embodiment, in which the strip 4 is provided with an S-shaped bend, is shown in FIG. 3f. The scored lines 5 are omitted in FIG. 3f for clarity reasons.

A fourth embodiment of the sensor 11 according to the disclosure corresponds to any of the above described embodiments except for the fact that one or more scored lines 5 is/are provided on each side 6, 7 of the strip 4, i.e. at least one scored line 5 is provided on the first side 6 and at least one scored line 5 is provided on the second side 7.

In a variant (not shown) of any of the above described embodiments of the sensor 11 according to the disclosure, the strip 4 is, instead of being coated with a layer 12 of a wetness sensitive polymer, coated directly or indirectly, i.e. with other layers such as suitable coupling layers in-between, on one of the first and second sides 6, 7 with at least one detector molecule adapted to detect at least one target biological and/or chemical analyte.

The detector molecule may in one embodiment be adapted to detect a biological or chemical analyte selected from the group consisting of an enzyme or a sequence of enzymes; an antibody; a nucleic acid, such as DNA or RNA; a protein, such as a soluble protein or a membrane protein; a peptide, such as an oligopeptide or a polypeptide; an organelle; parts of a natural or synthetic cell membrane or capside, such as a bacterial or a mammalian cell membrane, or a virus capside; an intact or partial viable or nonviable bacterial, plant or animal cell; a piece of plant or mammalian tissues or any other biologically derived molecule; a lipid, a carbohydrate; a lectin, and mixtures thereof.

In another embodiment the detector molecule may be adapted to detect a biological or chemical analyte selected from the group consisting of pathogenic bacteria; non-pathogenic bacteria, e.g. colonic bacteria; viruses; parasites; bacterial toxins; fungi; enzymes; proteins; peptides; mammalian blood cells, such as human white or red blood cells; hormones; mammalian, including human, blood components, such as blood glucose; urine and its components such as glucose, ketones, urobilinogen, and bilirubin; and mixtures thereof.

The bacteria that the detector molecule may be adapted to detect, pathogenic or not, is selected from the group consisting of *Escherichia coli, Salmonela typhi, Salmonella paratyphi, Salmonella enteriditid, Salmonella thyphimurium, Salmonella heidelberg, Staphylococcus aureus, Shigella sonnei, Shigella flexneri, Shigella boydii, Shigella dysenteriae, Vibrio cholerae, Mycobacterium tuberculosis, Yersina enterocolitica, Aeromonas hydrophila, Plesmonas shigelloides, Campylobacter jejuni, Campylobacter coli, Bacteroides fragilis, Clostridia septicum, Clostridia perfringens, Clostridia botulinum, Clostridia difficile*, and mixtures thereof.

In still another embodiment the detector molecule is adapted to detect a chemical compound or chemical analyte such as health markers or nutritional markers. Nutritional markers include markers for e.g. metabolic efficiency, nutrient deficiencies, nutrient absorption or malabsorption, food and drink intake, food allergies (e.g. to peanuts), food intolerance (e.g. lactose or gluten intolerance), colonic bacteria ecology (e.g. beneficial bacterias such as bifidobacteria and *lactobacillus*), and total energy balance. Health markers may include chemical analytes such as heavy metals (e.g. lead, mercury, etc.), radioactive substances (e.g. caesium, strontium, uranium, etc.), fats, enzymes, endogenous secretions, protein matter (e.g. blood casts), mucous, and micro-organisms, as described above, that may be related to various health issues such as infection, diarrhoea, gastrointestinal distress of disease, or poisoning. Heavy metals, especially in certain developing countries and in older and/or less affluent areas of developed countries, are serious health risks. For example, lead and mercury poisoning may occur upon the ingestion of these heavy metals from environmental sources (e.g. from lead paint, unregulated heavy industries, etc.) and can be fatal. More commonly, low-level poisoning by these and other heavy metals results in retarded intellectual and/or physical development, especially in children that may occur over a long time and have lasting effects on the individual. Other examples of nutritional markers include calcium, vitamins (e.g. thiamine, riboflavin, niacin, biotin, folic acid, pantothenic acid, absorbic acid, vitamin E, etc.), electrolytes (e.g. sodium, potassium, chlorine, bicarbonate, etc.), fats, fatty acids (long and short chain), soaps (e.g. calcium palmitate), amino acids, enzymes (e.g. lactose, amylase, lipase, trypsin, etc.), bile acids and salts thereof, steroids, and carbohydrates. For example, calcium malabsorption is important in that it may lead to a long-term bone-mass deficiency.

Suitable detector molecules may include any biorecognition element and are further exemplified by carbohydrates, antibodies or parts thereof, synthetic antibodies or parts thereof, enzymes, lectins, DNA (deoxyribonucleic acid), RNA (ribonucleic acid), cells and/or cell membranes or any other molecule with a binding capacity for a defined bioanalyte or chemical analyte.

For example, the detector molecules may be wholly or partially physiosorbed onto one of the first and second sides 6, 7 of the strip 4 using e.g. a cationic polymer such as polyethylene imine (PEI, from e.g. Sigma-Aldrich), a colloidal suspension such as polybead polystyrene (PS) microspheres (from e.g. Scientific Polymer Products), or a hydrophobic polymer such as polystyrene (from e.g. Scientific Polymer Products).

It is obvious to a person skilled in the art that any suitable means of applying the detector molecule than physiosorption onto one of the first and second sides 6, 7 of the strip 4 will be appropriate for other applications. For example, it may be desirable to chemically bind the detector molecule, directly or indirectly, to one of the first and second sides 6, 7 using any one of a variety of common crosslinker molecules including, but not limited to, glutaraldehyde, N-hydroxysuccinimide, carbodidimides.

When a detector molecule comprised in a sensor 11 according to the disclosure detects a biological and/or chemical analyte, the mass of the sensor 11 changes resulting in a change of the magnetoacoustic resonant frequency of the sensor 11, which is detectable.

In another variant of any of the above described embodiments of the sensor 11 according to the disclosure, the piece of a magnetoelastic material of the sensor 11 is not coated with any additional layer, such as a layer 12 of a wetness sensitive polymer, or any detector molecules. The sensor 11 may then, for example, be utilized in connection with position sensors.

As may be realized from the above, a strip 4 of a sensor 11 according to the present disclosure may be provided with any suitable number of scored lines 5. Furthermore, the scored line(s) 5 may be provided at any suitable position(s) on the strip 4 such that a suitable shape of a lasting bend is provided. In addition, the strip 4 may be provided with one or more scored lines 5 along which the strip 4 is not bent.

Furthermore, in variants of any of the above described embodiments, the piece of a film of a magnetoelastic material of the sensor 11 according to the disclosure has any other suitable shape than the shape of a strip. For example, the piece of a magnetoelastic material may then have the shape of a ribbon. In addition, even if the piece of a magnetoelastic material according to the disclosure in the embodiments described above has been provided with an enhanced bending stiffness in the longitudinal direction, it may in variants of any of the above described embodiments be provided with an enhanced bending stiffness in any other direction. The scored line(s) 5 is/are then provided in the direction in which an enhanced bending stiffness is provided.

As above described, a magnetoelastic material of a magnetoelastic sensor stores magnetic energy in a magnetoelastic mode when excited by an external magnetic field. When the magnetic field is switched off, the magnetoelastic material shows damped oscillation with a specific frequency denoted as the magnetoacoustic resonant frequency. These oscillations give rise to a magnetic flux that varies in time, which can be remotely detected by a pick-up coil. Thus, the magnetoacoustic resonant frequency is detectable and thereby also a change of the magnetoacoustic resonant frequency. If a pulsed magnetic field is applied to a magnetoelastic material, the magnetoacoustic resonant frequency may be detected between the magnetic pulses. The magnetoacoustic resonant frequency for e.g. a strip of a magnetoelastic material is inversely proportional to the length of the strip.

For example, a pulsed magnetic field or a pulsed sine wave magnetic field may be applied to the sensor 11 according to embodiments of the disclosure in order to detect the magnetoacoustic resonant frequency of the sensor 11. As mentioned above, the magnetoacoustic resonant frequency may then be detected between the pulses. The amplitude of the pulsed magnetic field must be large enough to magnetize the magnetoelastic material to a certain amount in order to achieve a sufficiently large change in material dimensions. The dimensions of the magnetoelastic material change due to the effect of magnetostriction. The specific magnetic field utilized must be optimised for each magnetoelastic material.

The pulse frequencies used may, for example, be about 10-1000 Hz, such as about 50-700 Hz. The duty cycles of the pulses may, for example, be about 1-90%, such as about 10-50%. If the magnetic field is a pulsed sine wave field, the sine waves may, for example, be about 50-80 kHz. If METGLAS® material from Honeywell is used as the magnetoelastic material, a magnetic field amplitude of the pulsing field may be about 0.05-0.1 mT.

An excitation coil may, for example, be utilized for applying a magnetic field to the magnetoelastic material of a sensor 11. A pick-up coil may, for example, be utilized for collecting the produced signal, i.e. the magnetoacoustic effect. The excitation coil and the pick-up coil may be located in a hand held unit. Furthermore, the excitation coil and the pick-up coil may be located in the same hand held unit or in different hand held units. In an alternative, the same coil may be utilized as both excitation coil and pick-up coil, i.e. both for excitation and detection. WO 2004/021944 is herein incorporated by reference in its entirety for further details regarding the excitation of the magnetoelastic material, detection of the magnetoacoustic resonant frequency as well as changes thereof and devices for detection of the magnetoacoustic resonant frequency.

One way of further enhancing the magnetostrictive effect of the magnetoelastic material in the sensor 11 according to the disclosure is to include a magnetic bias field. For example, a magnetic bias field may be generated by a permanent magnetic film or a permanent magnet positioned in proximity to the piece of a magnetoelastic material of the sensor 11. When METGLAS® material from Honeywell is used as the magnetoelastic material, a magnetic bias field of about 0.5-1 mT may be utilized.

A sensor 11 may be positioned in contact with or in spaced relation with an absorbent material of an absorbent structure of an absorbent article. For example, a sensor 11 may be comprised in an absorbent structure in an absorbent article, such as a diaper, a diaper of pant type, an incontinence garment, a sanitary napkin, a wipe, a towel, a tissue, a bed protector, a wound or sore dressing, a tampon-like product, or similar product. In normal use, an absorbent structure in such an absorbent article serves to absorb, retain and isolate body wastes or body exudates, e.g. urine, faeces, blood, menstruation blood, fluid matter from wounds and sores, rinsing fluid and saliva. When a sensor 11, in which the piece of a magnetoelastic material is at least partially coated with a layer 12 of a wetness sensitive polymer or at least one detector molecule, is comprised in such an absorbent structure it will enable easy detection of wetness or a biological and/or chemical analyte, i.e. it will enable easy detection of that an event such as urination or defecation has occurred. The detection is performed by detecting a change of the magnetoacoustic resonant frequency of the sensor 11. Thereby the status of the absorbent structure and, thus, of the absorbent article may be easily monitored by a user, parent, care taker, etc.

For example, a sensor 11, in which the piece of a magnetoelastic material is at least partially coated with a layer 12 of a wetness sensitive polymer or at least one detector molecule, may replace the sensing device disclosed in WO 2004/021944 and thus be comprised in the absorbent structures and absorbent articles disclosed in WO 2004/021944. Thus, such a sensor 11 may be positioned in different positions in an absorbent structure in accordance with the positions of the sensing device in WO 2004/021944 and an absorbent article may also comprise more than one such sensor 11. For example, an absorbent article may comprise 1-10 such sensors 11.

Figure 4:
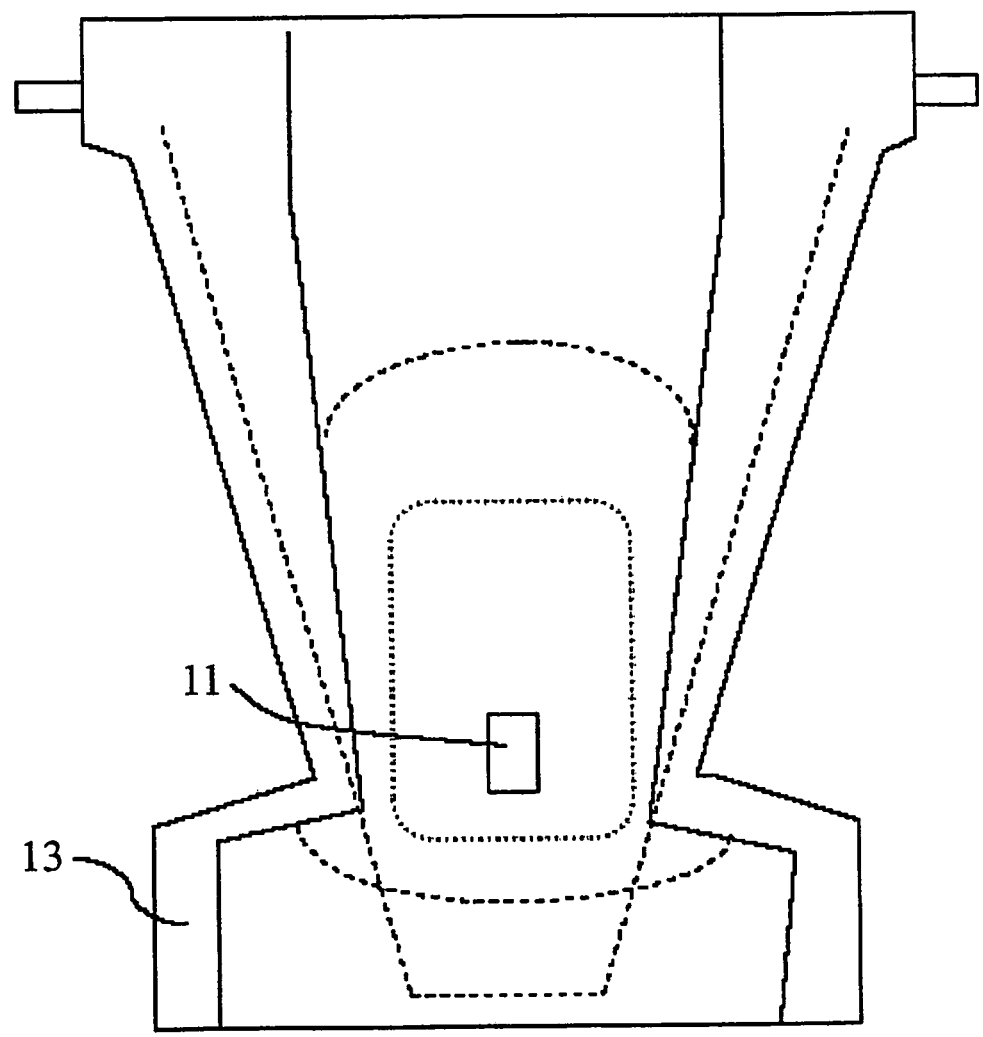
FIG. 4 shows schematically one non-limiting example of an absorbent article comprising a sensor according to the disclosure.

One non-limiting example of an absorbent article 13 comprising a sensor 11 is schematically shown in FIG. 4.

Optionally, the sensor 11 may be packaged or encapsulated accurately, not to be exposed to, e.g. mechanical pressure that may affect the resonant frequency or the magnetoacoustic resonant frequency. Then the sensor 11 may be packaged in a way that the wetness or at least one biological and/or chemical analyte can penetrate through the package into the sensor 11, e.g. via pores, slots or holes, in the package material. Suitable encapsulations include encapsulations in the form of tags such as tags from, e.g. Sensormatic, or a similar product. The encapsulations are designed or chosen in each case by a person skilled in the art to fit a specific embodiment.

Furthermore, if the sensor 11 does not comprise any wetness sensitive polymer or detector molecule, the sensor 11 may in one embodiment be encapsulated in an encapsulation together with an absorbing material, e.g. superabsorbent material (SAP). The encapsulation is then designed to allow liquid to penetrate into the encapsulation and the SAP will exert a mechanical pressure on the sensor 11 when absorbing liquid, moisture or humidity. The mechanical pressure correlates to the amount of e.g. liquid absorbed and will completely or partially dampen the oscillations of the sensor 11. A decrease in the magnetoacoustic effect will be detected when the oscillations are damped, whereby detection of liquid, moisture or humidity may be determined. WO 2004/021944 is herein incorporated by reference in its entirety for further details regarding the encapsulation in this embodiment and how this embodiment works.

Alternatively, if the sensor 11 does not comprise any wetness sensitive polymer or detector molecule, the sensor 11 may in another embodiment be comprised in an absorbent structure together with a permanent magnet. When the absorbent material of the absorbent structure swells due to uptake of a liquid, humidity or moisture, the absorbent material pushes the permanent magnet closer or away from the sensor 11. This will change the DC magnetic field on the sensor 11, whereby the magnetoacoustic oscillations are affected. WO 2004/021944 is herein incorporated by reference in its entirety for further details regarding the encapsulation in this embodiment and how this embodiment works.

In general terms, the sensor 11 comprises a piece 2, 4 of a film 1 of a magnetoelastic material, which piece 2, 4 has an initial bending stiffness in a first direction. The piece 2, 4 is provided with at least one scored line 5 in the first direction of the piece 2, 4. In addition, the piece 2, 4 is bent along at least one of said at least one scored lines 5 such that it is provided with a lasting bend in a direction transverse to the first direction. Due to the lasting bend, an enhanced bending stiffness is provided in the first direction of the piece 2, 4.

Thus, while there have been shown and described and pointed out fundamental novel features of the disclosure as applied to preferred embodiments thereof, it will be understood that various omissions and substitutions and changes in the form and details of the devices, method steps and products illustrated may be made by those skilled in the art. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. It is the intention, therefore, to be limited only as indicated by the scope of the claims appended hereto, and equivalents thereof.

The invention claimed is:

1. A method for providing a piece of a film of a magnetoelastic material having an initial bending stiffness with an enhanced bending stiffness in a first direction, the method comprising the steps of:
   a. providing said piece with at least one scored line in said first direction of said piece, and
   b. bending said piece along at least one of said at least one scored line so as to provide said piece with a lasting bend in a direction transverse to said first direction, whereby an enhanced bending stiffness is provided in said first direction of said piece,
   wherein said piece is provided with said at least one scored line by an etching process, said etching process being one of a chemical process, an electrochemical process, an ion beam process or a photo etching process.

2. The method according to claim 1, wherein said piece is a strip and that said first direction is the longitudinal direction of the strip.

3. The method according to claim 1, wherein said piece is bent along at least one of said at least one scored line by a mould such that the magnetoelastic material is at least partially plastically deformed at a bottom of the at least one scored line along which the piece is bent.

4. The method according to claim 1, wherein said piece in said step of bending is bent so as to provide said piece with a lasting bend being curve-shaped, wave-shaped, angular, right-angular, V-shaped, L-shaped, U-shaped or S-shaped.

5. A product comprising a piece of a film of a magnetoelastic material, which product is obtained by a method according to claim 1.

6. The method according to claim 1, wherein said scored line is a single scored line provided substantially in a center in said first direction of said piece.

7. The method according to claim 1, wherein said piece is provided with at least one scored line in said first direction of said piece on a first side of said piece and provided with at least one scored line in said first direction on a second side of said piece.

8. The method according to claim 1, wherein a depth of said scored line is 10 to 20% of thickness of the film.

9. A sensor comprising a piece of a film of a magnetoelastic material, which piece has an initial bending stiffness in a first direction, wherein said piece is provided with at least one scored line in said first direction of said piece and that said piece is bent along at least one of said at least one scored line such that said piece is provided with a lasting bend in a direction transverse to said first direction, whereby an enhanced bending stiffness is provided in said first direction of said piece,
   said piece coated with a detection layer on one side, wherein another side is uncoated, the at least one scored line being provided on the side that is not coated.

10. The sensor according to claim 9, wherein said piece is a strip and that said first direction is the longitudinal direction (y) of said strip.

11. The sensor according to claim 9, wherein said lasting bend is curve-shaped, wave-shaped, angular, right-angular, V-shaped, L-shaped, U-shaped or S-shaped.

12. The sensor according to claim 9, wherein said detection layer is a wetness sensitive polymer is selected from the group consisting of linear and hydrophilic polymers or chemically/physically cross-linked swellable polymer gels based on polyvinyl alcohol, polyvinyl pyrrolidone, polyethylene oxide and co-polymers thereof, polyurethane, polyamides, starch and derivatives thereof, cellulose and derivatives thereof, polysaccharides, proteins, polyacrylonitrile, polyethylene imine, acrylate based polymers, and mixtures thereof.

13. The sensor according to claim 9, wherein said detection layer is at least one detector molecule adapted to detect at least one target biological and/or chemical analyte.

14. An absorbent structure comprising at least one absorbent layer, wherein the absorbent layer comprises the sensor according to claim 9.

15. An absorbent article comprising the sensor according to claim 9.

16. The absorbent article according to claim 15, wherein the article comprises 2-10 sensors according to claim 9.

17. A sensoring absorbent system comprising a hand held unit, the hand held unit comprising an excitation coil generating a magnetic field to magnetize said magnetoelastic material wherein the sensoring absorbent system further comprises the absorbent structure according to claim 14.

* * * * *